(12) United States Patent
Kim et al.

(10) Patent No.: US 9,793,489 B2
(45) Date of Patent: Oct. 17, 2017

(54) PYRENE COMPOUND AND ORGANIC LIGHT EMITTING DIODE DEVICE INCLUDING THE SAME

(71) Applicant: LG DISPLAY CO., LTD., Seoul (KR)

(72) Inventors: Shinhan Kim, Goyang-si (KR); Jeongdae Seo, Incheon (KR); Hyoseok Kim, Daejeon (KR); Youngkwan Jung, Daegu (KR); Eunju Jeon, Icheon-si (KR)

(73) Assignee: LG DISPLAY CO., LTD., Seoul (KR)

( * ) Notice: Subject to any disclaimer, the term of this patent is extended or adjusted under 35 U.S.C. 154(b) by 0 days.

(21) Appl. No.: 14/831,638

(22) Filed: Aug. 20, 2015

(65) Prior Publication Data

US 2015/0357577 A1    Dec. 10, 2015

Related U.S. Application Data

(63) Continuation of application No. 13/725,400, filed on Dec. 21, 2012, now Pat. No. 9,147,846.

(30) Foreign Application Priority Data

Sep. 3, 2012 (KR) .................. 10-2012-0097357

(51) Int. Cl.
| | | |
|---|---|---|
| H01L 51/00 | (2006.01) |
| H01L 51/50 | (2006.01) |
| H01L 27/32 | (2006.01) |
| C07D 215/12 | (2006.01) |
| C07D 519/00 | (2006.01) |

(Continued)

(52) U.S. Cl.
CPC ........ *H01L 51/0054* (2013.01); *C07D 213/06* (2013.01); *C07D 213/16* (2013.01);
(Continued)

(58) Field of Classification Search
None
See application file for complete search history.

(56) References Cited

U.S. PATENT DOCUMENTS 5,079,118 A     1/1992  Kikuchi et al.
2004/0209118 A1*  10/2004  Seo ................. C09K 11/06
                                               313/504

(Continued)

FOREIGN PATENT DOCUMENTS

CN    101003508 A    7/2007
CN    101258221 A    9/2008

(Continued)

OTHER PUBLICATIONS

Pyrene-Bridged Bis(phenanthroline) Ligands and Their Dinuclear Ruthenium(n) Complexes by Latif Chouai, Feiyue Wu, Youngchan Jang, and Randolph P. Thummel, Dec. 2003.*

(Continued)

*Primary Examiner* — Marc Armand
*Assistant Examiner* — Quinton Brasfield
(74) *Attorney, Agent, or Firm* — Seed Intellectual Property Law Group LLP (57) ABSTRACT

A pyrene compound and an organic light emitting diode device including the same are disclosed. The organic light emitting diode device includes at least two stacks provided between a first electrode and a second electrode, and a charge generation layer provided between the stacks and including an N type charge generation layer and a P type charge generation layer, wherein the N type charge generation layer is made of the pyrene compound.

6 Claims, 3 Drawing Sheets

(51) Int. Cl.
- C07D 401/14 (2006.01)
- C07D 215/04 (2006.01)
- C07D 401/10 (2006.01)
- C07D 471/04 (2006.01)
- C07D 213/06 (2006.01)
- C07D 213/16 (2006.01)
- C09B 57/00 (2006.01)
- H01L 51/52 (2006.01)

(52) U.S. Cl.
CPC ......... *C07D 215/04* (2013.01); *C07D 215/12* (2013.01); *C07D 401/10* (2013.01); *C07D 401/14* (2013.01); *C07D 471/04* (2013.01); *C07D 519/00* (2013.01); *C09B 57/001* (2013.01); *H01L 27/3211* (2013.01); *H01L 51/0052* (2013.01); *H01L 51/0067* (2013.01); *H01L 51/0072* (2013.01); *H01L 51/5012* (2013.01); *H01L 51/5044* (2013.01); *H01L 51/5278* (2013.01); *H01L 51/0058* (2013.01); *H01L 51/5036* (2013.01); *H01L 51/5056* (2013.01); *H01L 51/5072* (2013.01); *H01L 51/5088* (2013.01); *H01L 51/5092* (2013.01); *H01L 51/5206* (2013.01); *H01L 51/5221* (2013.01)

(56) References Cited

U.S. PATENT DOCUMENTS

| | | | |
|---|---|---|---|
| 2007/0167626 | A1 | 7/2007 | Kim et al. |
| 2008/0012475 | A1* | 1/2008 | Oyamada ............ C07C 13/567 313/504 |
| 2008/0015399 | A1 | 1/2008 | Funahashi |
| 2008/0269491 | A1 | 10/2008 | Jabbour et al. |
| 2011/0198582 | A1 | 8/2011 | Horiuchi et al. |
| 2012/0032152 | A1* | 2/2012 | Kim ..................... C07C 211/58 257/40 |
| 2012/0098011 | A1* | 4/2012 | Choi .................. H01L 27/3209 257/98 |

FOREIGN PATENT DOCUMENTS

| | | |
|---|---|---|
| CN | 101550234 A | 10/2009 |
| CN | 103178212 A | 6/2013 |

OTHER PUBLICATIONS

Pyrene-Bridged Bis(phenanthroline) Ligands and Their Dinuclear Ruthenium(n) Complexes by Latif Chouai, Feiyue Wu, Youngchan Jang, and Randolph P. Thummel Dec. 2003.*

Bonnefous et al., "Cyclometalated Complexes of Ru(II) with 2-Aryl Derivatives of Quinoline and 1,10-Phenanthroline" Inorg. Chem. 40, 2001, pp. 5851-5859.

Tyson et al., "Excited State Processes in Ruthenium(II)/Pyrenyl Complexes Displaying Extended Lifetimes" J. Phys. Chem. A 105, 2001, pp. 8154-8161.

Office Action issued in Chinese Patent Application No. 201210595827.2, mailed Nov. 25, 2014, 16 pages.

Chouai, Latif et al., "Pyrene-Bridged Bis(phenathroline) Ligands and Their Dinuclear Ruthenium(II) Complexes," Eur. J. Inorg. Chem, 2003, pp. 2774-2782.

Office Action dated May 19, 2015 for corresponding Chinese Application No. 201210595827.2, 13 pages.

* cited by examiner

PYRENE COMPOUND AND ORGANIC LIGHT EMITTING DIODE DEVICE INCLUDING THE SAME

This application is a continuation application of U.S. patent application Ser. No. 13/725,400, filed on Dec. 21, 2012, which claims the benefit of Korean Patent Application No. 10-2012-0097357 filed on Sep. 3, 2012, which is incorporated herein by reference for all purposes as if fully set forth herein.

BACKGROUND

Field of the Disclosure

This document relates to an organic light emitting diode device, and more particularly, to an organic light emitting diode device including a pyrene compound.

Discussion of the Related Art

In recent years, with the development of multi-media, the importance of a flat panel display (FPD) has increased. To satisfy the demand, various displays such as a liquid crystal display (LCD), a plasma display panel (PDP), a field emission display (FED), and an organic light emitting diode device have been put to practical use.

Particularly, the organic light emitting diode device is a self-emissive device, which represents fast response speed of 1 ms or less and low power consumption. Further, since the organic light emitting diode device has an excellent viewing angle, the organic light emitting diode device is beneficial as a moving picture display medium regardless of the size of a device. In addition, since the organic light emitting diode device may be fabricated at a low temperature and a manufacturing process thereof is simple based on an existing semiconductor process technique, it is spotlighted as a next-generation flat panel display.

The organic light emitting diode device includes a cathode, an anode and an organic emission layer interposed between the cathode and the anode. An electron provided from the cathode is combined with a hole provided from the anode at the emission layer to form an exciton. The exciton is transited into a ground state from an excited state, thereby emitting light.

The organic light emitting diode device has been developed as various structures. Among them, a tandem organic light emitting diode device manufacturing by stacking a plurality of emission layers has been developed. The organic light emitting diode device has a plurality of stack structures including a hole injection layer/hole transport layer/emission layer/electron transport layer/electron injection layer. Particularly, a charge generation layer including N type and P type charge generation layers is formed between the stacks, so that a charge is generated or the charge is injected into each emission layer.

However, in the charge generation layer, an injection characteristic of an electron generated by charge generation at an interfacial surface of a hole injection layer adjacent to a P type charge generation layer due to an energy level difference between an N type charge generation layer and the P type charge generation layer in the N type charge generation layer is deteriorated. When the N type charge generation layer according to the related art is doped with alkaline metal, the alkaline metal is diffused into the P type charge generation layer so that life span of the device is deteriorated.

SUMMARY

A pyrene compound is represented by the following chemical formula 1:

[Chemical formula 1]

in the chemical formula 1, the A is one selected from C, N, S, and O, the B and R1 are one selected from a hetero aromatic group having 6 to 24 carbon atoms which includes or does not include a neighboring A, a substituted or unsubstituted aromatic arylamine group, or a substituted or unsubstituted hetero aromatic arylamine group, and the n is an integer in the range of 1 to 4. In another aspect, there is an organic light emitting diode device including at least two stacks provided between a first electrode and a second electrode and a charge generation layer provided between the stacks and including an N type charge generation layer and a P type charge generation layer, wherein the N type charge generation layer is made of the pyrene compound.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION

Reference will now be made in detail to embodiments of the invention, examples of which are illustrated in the accompanying drawings. Wherever possible, the same reference numbers will be used throughout the drawings to refer to the same or like parts. It will be paid attention that detailed description of known arts will be omitted if it is determined that the arts can mislead the embodiments of the invention.

Figure 1:
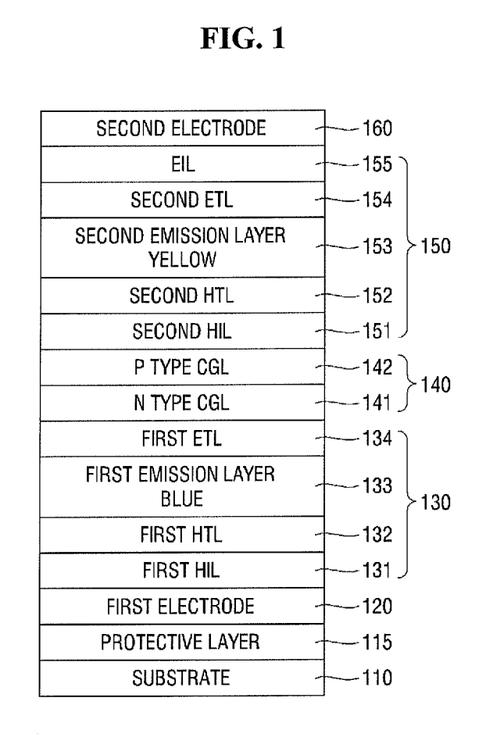
FIG. 1 is a view illustrating an organic light emitting diode device according to an exemplary embodiment of the present invention.

FIG. 1 is a view illustrating an organic light emitting diode device according to an exemplary embodiment of the present invention. Hereinafter, an organic light emitting diode device in which two stacks are laminated is described by way of example, but the present invention is not limited thereto.

Referring to FIG. 1, the organic light emitting diode device 100 according to an exemplary embodiment of the present invention may be a white organic light emitting diode device having yellow and blue lights. In detail, the organic light emitting diode device 100 includes a first electrode 120 on a substrate 110, a first stack 130 disposed on the first electrode 120 and including a first emission layer 133, a charge generation layer 140 disposed on the first stack 130, a second stack 150 disposed on the charge generation layer 140 and including a second emission layer 153, and a second electrode 160 disposed on the second stack 150.

The substrate 110 may be made of transparent glass and plastic material, or conductive material. The first electrode 120 is an anode electrode injecting a hole and may be a transparent electrode transmitting light. The first electrode 120 is configured by one of Indium Tin Oxide (ITO), Indium Zinc Oxide (IZO), or Zinc Oxide (ZnO). The organic light emitting diode device 100 may include a protective layer 115 between the substrate 100 and the first electrode 120. The protective layer 115 reflects light upward and may be made of one aluminum (Al), silver (Ag), and nickel (Ni) at a lower portion of the first electrode 120.

The first stack 130 disposed on the first electrode 120 may include a first emission layer 133 emitting blue light. The first stack 130 may include only a blue emission layer as the first emission layer 133 and emit blue light to increase color stability of blue. The first emission layer 133 is an emission layer emitting blue light, and a fluorescent blue dopant may be mixed with one host. For example, the first emission layer 130 may be formed by mixing 1,6-Bis(diphenylamine) pyrene or TBPe(tetrakis(t-butyl)perylene) being a fluorescent blue dopant with a host material such as AND(9,10-di (2-naphthyl)anthracene) or DPVBi(4,4'-bis(2,2-diphenylethen-1-yl)-diphenyl). The fluorescent blue dopant may be a deep or sky blue dopant. For example, the deep blue dopant may include 4'-N,N-diphenylaminostyryl-triphenyl (DPA-TP), 2,5,2',5'-tetrastyryl-biphenyl (TSB), or anthracene derivative.

For example, the sky blue dopant may include p-bis(p-N,N-diphenyl-aminostylrl) bezene or phenyl cyclopentadiene.

The first stack 130 may further include a first hole injecting layer (HIL) 131 formed between the first electrode 120 and the first emission layer 133, and a first electron transport layer (HTL) 134 formed between the first emission layer 133 and the charge generation layer 140.

The first HIL 131 may easily inject a hole from the first electrode 120 to the first emission layer 133. The first HIL 131 may be made of at least one selected from the group consisting of cupper phthalocyanine (CuPc), poly(3,4)-ethylenedioxythiophene (PEDOT), polyaniline (PANI), and N,N-dinaphthyl-N,N'-diphenyl benzidine (NPD), but the present invention is not limited thereto.

The first HTL 132 functions to easily transport a hole. The first HTL 132 may be made of at least one selected from the group consisting of N,N-dinaphthyl-N,N'-diphenyl benzidine (NPD), N,N'-bis-(3-methylphenyl)-N,N'-bis-(phenyl)-benzidine (TPD), s-TAD, and (4,4',4"-Tris(N-3-methylphenyl-N-phenyl-amino)-triphenylamine (MTDATA), but the present invention is not limited thereto.

The first electron transport layer (ETL) 134 functions to easily transport an electron. The first ETL 134 may be made of at least one selected from the group consisting of tris(8-hydroxyquinolino)aluminum) (Alq3), PBD, TAZ, spiro-PBD, BAlq, and SAlq, but the present invention is not limited thereto.

Meanwhile, a charge generation layer (CGL) 140 disposed on the first stack 130 is a PN junction charge generation layer where a junction is formed between an N type charge generation layer 141 and a P type charge generation layer 142. The PN junction CGL 140 generates and injects the charge to the respective emission layers or separately injects a hole and an electron into each emission layer. That is, the N type CGL 141 supplies an electron to the first emission layer 133 adjacent to the first electrode 120 and the P type CGL 142 supplies a hole to the second emission layer 153 adjacent to the second electrode 160, so that luminous efficiency of the organic light emitting diode device including a plurality of emission layers may be increased and a driving voltage may be reduced.

The N type CGL 141 is made of pyrene compound, and a detailed description thereof will be described below. The P type CGL 142 may be made of metal or an organic material doped with a P type dopant. Here, the metal may include one selected from the group consisting of Al, Cu, Fe, Pb, Zn, Au, Pt, W, In, Mo, Ni, and Ti, and an alloy thereof. A P type dopant and a host material used in an organic material doped with the P type dopant may use a generally used material. For example, the P type dopant may be one material selected from the group consisting of 2,3,5,6-tetrafluoro-7,7,8,8-tetracyanoquinodimethane (F4-TCNQ), a derivative of tetracyanoquinodimethane, iodine, $FeCl_3$, $FeF_3$, and $SbCl_5$. Further, the host may be one material selected from the group consisting of N,N'-D(naphthalene-1-1)-N,N-diphenyl-benzidine (NPB), N,N'-diphenyl-N,N'-bis(3-methylphenyl)-1,1-biphenyl-4,4'-diamine (TPD), and N,N',N'-tetranaphthyl-benzidine (TNB).

The second stack 150 disposed on the CGL 140 may include the second emission layer 153 emitting yellow light. The second emission layer 153 may include a yellow dopant in a host or red and green dopants in one host.

For example, when the second emission layer 153 includes the yellow dopant in the host, the second emission layer 153 may use the same material as that of the host of the first emission layer 133 as the host and a blue dopant, and may use Irpq2acac(bis(phenylquinoline) iridium acetylacetonate). Further, when the second emission layer 153 includes red and green dopants in one host, Ir(piq)2acac(bis (phenylisoquinoline) iridium acetylacetonate) may be used in the foregoing host as a red phosphoresce dopant. An Irppy3(tris(phenylpyridine) iridium) may be used as the red phosphoresce dopant.

The second stack 150 may further include a second hole injection layer 151 and a second hole transport layer 153 formed between the CGL 140 and the second emission layer 153, and a second electron transport layer 154 and an electron injection layer (EIL) 155. The second hole injection layer 151, the second hole transport layer 152, and the second electron transport layer 154 have the same functions as those of the first hole injection layer 131, the first hole transport layer 132, and the first electron transport layer 134, and thus the description thereof is omitted.

The EIL 155 functions to easily inject an electron, and may use Alq3(tris(8-hydroxyquinolino)aluminum), PBD, TAZ, spiro-PBD, BAlq, or SAlq, but the present invention is not limited thereto. In addition, the EIL 155 may be made of a metal halide compound. For example, the metal halide compound may be one selected from the group consisting of $MgF_2$, LiF, NaF, KF, RbF, CsF, FrF, and $CaF_2$, but the present invention is not limited thereto.

The second electrode (cathode) 160 may be mode of a transparent material so that light emitted from the emission layers 133 and 135 may be outputted to a front surface. For example, the second electrode 160 may be made of one of indium tin oxide (ITO), indium zinc oxide (IZO), and zinc oxide (ZnO).

The N type CGL 141 of the present invention may be made of a pyrene compound represented as a following chemical formula 1.

[Chemical formula 1]

In the chemical formula 1, the A is one selected from C, N, S, and O, the B and R1 are one selected from a hetero aromatic group having 6 to 24 carbon atoms which includes or does not include a neighboring A, a substituted or unsubstituted aromatic arylamine group, or a substituted or unsubstituted hetero aromatic arylamine group, and the n is an integer in the range of 1 to 4.

The R1 neighboring the B including the A forms or does not form a fused ring.

The chemical formula 1 is represented as following chemical formulas 2 to 8.

[Chemical formula 2]

[Chemical formula 3]

[Chemical formula 4]

[Chemical formula 5]

[Chemical formula 6]

[Chemical formula 7]

[Chemical formula 8]

In the chemical formulas 2 to 8, each substituent may form a fused ring with a neighboring substituent.

The compound represented as the chemical formula 1 is expressed as compounds of following P1 to P26.

P1

P2

P13

P14

P15

P16

P17

P18

P19

P20

At least one substituent in the chemical formula 1 is substituted in numbers 1, 3, 6, and 8 locations of a pyrene.

Since number 2 and 6 locations of the pyrene in the chemical formula 1 are easily substituted and there is a π interacted carbon in a beta location from a substituted location, an orbital associated with π interaction of the carbon may be used in interaction with transition metal.

In detail, referring to a following chemical formula 9, when lithium (Li) is doped with an N type dopant, a site having a rich electron is positioned at a location B, so that the lithium (Li) doped with the N type dopant easily interacts with lithium being a system having a relatively deficient electron that enables stronger interaction while forming the chemically stablest hexagonal ring shape. In this case, a location A directly donates the electron or functions a linker of donating.

[Chemical formula 9]

Hereinafter, a synthesis example of the pyrene compound used for the N type CGL of the present invention and the organic light emitting diode device including the same will be described with reference to a following synthesis example and embodiment. However, embodiments will be described by way of example only, and the present invention is not limited to following embodiments.

SYNTHESIS EXAMPLE

1) Synthesis of 2,4-dibromo-9-phenyl-9H-carbazole(B)

[Reaction formula 1]

Prepared Example: Synthesis of Dibromo Pyrene

A first solution including bromine 16 g and chloroform 100 ml was dropped in a second solution obtained by solving pyrene 10.0 g (49.4 mmol) in chloroform 250 ml while agitating the second solution at a temperature of 23° C. for 7 hours. After additionally agitating the second solution for one hour, an obtained reaction liquid (including crystal) was filtered so that a crystal was obtained. A dibromo pyrene 11.3 g is obtained by washing the crystal and then drying the washed crystal under reduced pressure (yield 63%) GC-Mass (theoretical value: 283.16 g/mol, measured value: 282 g/mol).

2) Manufacture of Compound A: Synthesis of 1,6-di(quinolin-3-yl)pyrene (A)

[Reaction formula 2]

A

Quinoline-3-boronic acid (2.2 g, 12.2 mmol), trioctylmethylammonium chloride (trademark name: Aliquat336 (hereinafter referred to as ⌜Aliquat336⌟), prepared by Aldrich Corporation, 0.74 g), palladium acetate (1.3 mg), tris(o-methoxyphenyl)phosphine (13.3 mg), toluene (58 ml), and sodium carbonate water solution (17.8 mmol) were added to dibromo pyrene (2.0 g, 5.6 mmol) synthesized in the prepared example and they were agitated at a temperature of 100° C. of four hours. A crystal was obtained by cooling the resultant reaction liquid at room temperature and filtering the cooled reaction (including the crystal). The compound A of 1.2 g was obtained by washing the crystal in an order of toluene, water, and methanol, and drying the washed crystal under reduced pressure (yield 46%).

GC-Mass (theoretical value: 456.16 g/mol, measured value: 456 g/mol), 1H-NMR (THF-d8, 500 MHz) (ppm) 7.58 (m, 2H), 7.68~7.74 (m, 8H), 8.04~8.06 (m, 4H), 8.22 (m, 2H), 9.03 (m, 2H)

3) Manufacture of Compound B: Synthesis of 1,6-di(quinolin-8-yl)pyrene (B)

[Reaction formula 3]

-continued

B

Quinoline-8-boronic acid (2.2 g, 12.2 mmol), trioctylmethylammonium chloride (trademark name: Aliquat336 (hereinafter referred to as ⌜Aliquat336⌟), prepared by Aldrich Corporation, 0.74 g), palladium acetate (1.3 mg), tris(o-methoxyphenyl)phosphine (13.3 mg), toluene (58 ml), and sodium carbonate water solution (17.8 mmol) were added to dibromo pyrene (2.0 g, 5.6 mmol) synthesized in the prepared example and they were agitated at a temperature of 100° C. of four hours. A crystal was obtained by cooling the resultant reaction liquid at room temperature and filtering the cooled reaction (including the crystal). The compound B of 1.8 g was obtained by washing the crystal in an order of toluene, water, and methanol, and drying the washed crystal under reduced pressure (yield 48%).

GC-Mass (theoretical value: 456.16 g/mol, measured value: 456 g/mol), 1H-NMR (THF-d8, 500 MHz) (ppm) 7.49~7.71 (m, 10H), 7.83 (m, 2H), 8.00~8.06 (m, 6H), 8.81 (m, 2H)

4) Manufacture of Compound C: Synthesis of 1,6-di(1,10-phenanthrolin-5-yl)pyrene (C)

[Reaction formula 4]

C 1,10-phenenthrene-5-boronic acid (2.2 g, 12.2 mmol), trioctylmethylammonium chloride (trademark name: Aliquat336 (hereinafter referred to as ⌜Aliquat336⌟), prepared by Aldrich Corporation, 0.74 g), palladium acetate (1.3 mg), tris(o-methoxyphenyl)phosphine (13.3 mg), toluene (58 ml), and sodium carbonate water solution (17.8 mmol) were added to dibromo pyrene (2.0 g, 5.6 mmol) synthesized in the prepared example and they were agitated at a temperature of 100° C. of four hours. A crystal was obtained by cooling the resultant reaction liquid at room temperature and filtering the cooled reaction (including the crystal). The compound C of 2.4 g was obtained by washing the crystal in an order of toluene, water, and methanol, and drying the washed crystal under reduced pressure (yield 77%).

GC-Mass (theoretical value: 558.63 g/mol, measured value: 558 g/mol), 1H-NMR (THF-d8, 500 MHz) (ppm) 7.26 (m, 2H), 7.55 (m, 2H), 7.71~7.77 (m, 6H), 8.00~8.06 (m, 8H), 8.80 (m, 4H)

Comparative Example

Hereinafter, disclosed is an embodiment of fabricating an organic light emitting diode device using a pyrene compound prepared in the foregoing synthesis example as an N type CGL.

A layer structure of the embodiment is the same as that of the comparative example to be described below. The difference is that a host material of the N type CGL is compounds A, B, C and B-phen(4,7-diphenyl-1,10-phenanthroline). First, a first electrode was formed on a transparent substrate by indium tin oxide (ITO) being an anode material. N,N'-diphenyl-N,N'-bis-[4-(phenyl-m-tolylamino)-phenyl]-biphenyl-4,4'-diamine having a thickness of 10 nm is formed on the first electrode to form a hole injection layer. NPD (4,4'-bis[N-(1-naphthyl)-N-phenylamino]-biphenyl) (N,N'-diphenyl-N-naphthyl-N'-biphenyl-1,1-biphenyl-4,4"-diamine) having a thickness of 100 nm was deposited on the hole injection layer to form a hole transport layer. An emission layer having a thickness of 200 Å including a fluorescent blue dopant in a fluorescent host material expressed in a following exemplary molecule 1 was formed on the hole transport layer. An electron transport layer was formed on the emission layer by depositing Alq3 having a thickness of 350 Å, and a CGL was formed on the electron transport layer. In this case, the CGL is divided into two layers which are an N type layer and a P type layer. The N type layer is formed by co-depositing B-phen(4,7-diphenyl-1,10-phenanthroline) expresses by a following exemplary molecule 2 and metal dopant lithium with a volume ratio of 1% to 50%. The P type was formed by depositing HAT-CN (dipyrazino[2,3-f:2',3'-h]quinoxaline-2,3,6,7,10,11-hexacarbonitril) represented as a following exemplary molecule 3 having a thickness of 100 Å. Finally, a second electrode as a cathode was formed on the CGL by using protective metal such as Al.

<Exemplary molecule 1>

<Exemplary molecule 2>

<Exemplary molecule 3>

Example 1

Under the same process conditions as those of the comparative example, an N type CGL is formed using the foregoing prepared compound A instead of B B-phen(4,7-diphenyl-1,10-phenanthroline) represented as the exemplary molecule 2.

Example 2

Under the same process conditions as those of the comparative example, an N type CGL is formed using the foregoing prepared compound B instead of B B-phen(4,7-diphenyl-1,10-phenanthroline) represented as the exemplary molecule 2.

Example 3

Under the same process conditions as those of the comparative example, an N type CGL is formed using the foregoing prepared compound C instead of B B-phen(4,7-diphenyl-1,10-phenanthroline) represented as the exemplary molecule 2.

Figure 2:
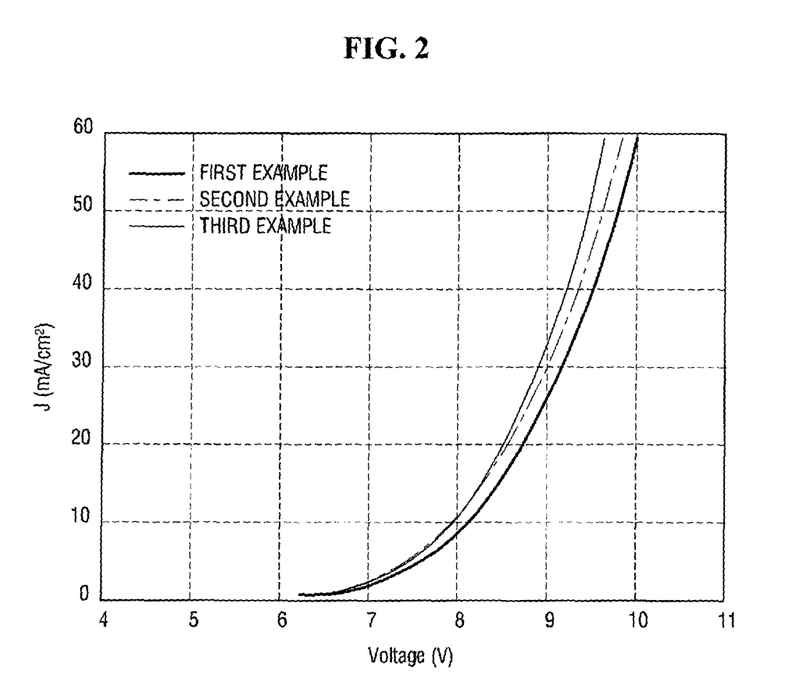
FIG. 2 is a graph illustrating a current density according to a driving voltage of the organic light emitting diode device fabricated according to an exemplary embodiment of the present invention.

Driving voltages, current efficiencies, quantum efficiencies, color coordinates, and life spans of the organic light emitting diode device according to the first to third embodiments and the comparative example are measured and listed in a following table 1. Further, current densities according to driving voltages are measured and illustrated in FIG. 2, and a deterioration rate of luminance according to a time is measured and illustrated in FIG. 3.

TABLE 1

| | Driving voltage (V) | Current efficiency (cd/A) | Quantum efficiency cy (%) | Color coordinates | | Life span (T80, hr) |
| --- | --- | --- | --- | --- | --- | --- |
| | | | | CIE_x | CIE_y | |
| Example 1 | 6.0 | 6.8 | 7.4 | 0.135 | 0.105 | 220 |
| Example 2 | 6.6 | 6.8 | 7.6 | 0.135 | 0.102 | 190 |
| Example 3 | 6.3 | 6.6 | 7.1 | 0.135 | 0.106 | 80 |
| Comparative example | 5.9 | 6.6 | 7.0 | 0.134 | 0.109 | 160 |

Figure 3:
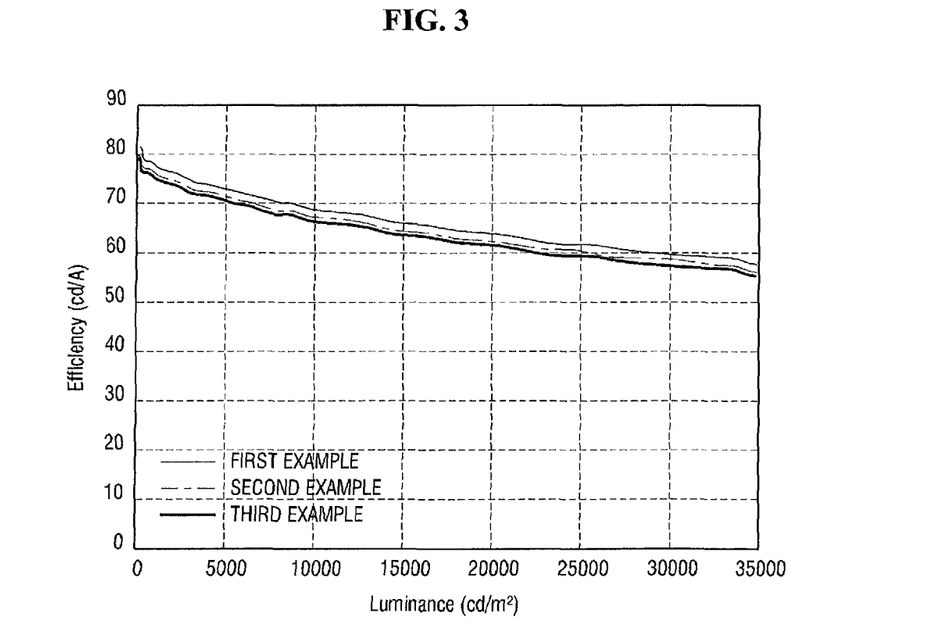
FIG. 3 is a graph showing a life span deterioration ratio according a time of according to the organic light emitting diode device fabricated according to an exemplary embodiment of the present invention.

As listed in the table 1, it will be appreciated that the organic light emitting diode device fabricated according the first to third embodiments of the present invention can significantly improve quantum efficiency while representing color coordinates of the same level as that of the comparative example. Particularly, referring to FIG. 2, the current density according to the driving voltage is improved, and a life span characteristic is significantly improved as shown in FIG. 3.

Therefore, the pyrene compound and the organic light emitting diode device including the same according to the embodiment of the present invention can improve the quantum efficiency and the life span characteristic as compared with an organic light emitting diode device according to the related art.

Although embodiments have been described with reference to a number of illustrative embodiments thereof, it should be understood that numerous other modifications and embodiments can be devised by those skilled in the art that will fall within the scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A pyrene compound represented by one of the following compounds:

2. An organic light emitting diode device comprising:
at least two stacks provided between a first electrode and a second electrode; and
a charge generation layer provided between the stacks and including an N type charge generation layer and a P type charge generation layer,
wherein the N type charge generation layer is made of the pyrene compound represented by one of the following compounds:

3. The organic light emitting diode device of claim 2, wherein each of the stacks comprises a hole injection layer and a hole transport layer formed at one side of the stack and an electron transport layer formed at an opposite side of the stack, while being interposed an emission layer therebetween.

4. The organic light emitting diode device of claim 2, wherein stacks adjacent to the second electrode among the stacks further comprise an electron injection layer.

5. The organic light emitting diode device of claim 2, wherein emission layers of the stacks emit lights of different colors, respectively.

6. The organic light emitting diode device of claim 2, wherein the N type charge generation layer is doped with alkaline metal.

* * * * *